United States Patent [19]

M'Timkulu et al.

[11] Patent Number: 5,578,310
[45] Date of Patent: Nov. 26, 1996

[54] TOPICAL BIOADHESIVE OINTMENT COMPOSITIONS AND THEIR USE IN WOUND HEALING

[75] Inventors: Thabiso M'Timkulu, El Sobrante; Ze'ev Shaked, Berkeley; Richard Hsu, Union City, all of Calif.

[73] Assignee: Berlex Laboratories Inc.

[21] Appl. No.: 253,472

[22] Filed: Jun. 3, 1994

(Under 37 CFR 1.47)

Related U.S. Application Data

[63] Continuation-in-part of Ser. No. 872,755, Apr. 23, 1992, abandoned.

[51] Int. Cl.$^6$ .......................... A61K 9/107; A61K 47/44; A61K 47/38; A61K 47/34
[52] U.S. Cl. .......................... 424/401; 424/434; 424/436; 424/455; 424/486; 514/939; 514/941; 514/969; 514/928
[58] Field of Search .......................... 424/401, 434, 424/436, 488, 489, 443, 486; 514/939, 941, 969

[56] References Cited

U.S. PATENT DOCUMENTS

| | | | |
|---|---|---|---|
| 3,818,105 | 6/1974 | Coopersmith et al. | 424/358 |
| 4,393,061 | 7/1983 | Yu | 424/248.58 |
| 4,436,848 | 3/1984 | Haines et al. | 523/426 |
| 4,464,202 | 8/1984 | Andres et al. | 106/139 |
| 4,708,873 | 11/1987 | Schulte | 424/195.1 |
| 4,867,970 | 9/1989 | Newsham et al. | 424/81 |
| 4,874,746 | 10/1989 | Antoniades et al. | 514/21 |
| 4,929,442 | 5/1990 | Powell | 424/85.2 |
| 5,061,700 | 10/1991 | Dow et al. | 514/169 |
| 5,063,060 | 11/1991 | Bernstein | 424/422 |
| 5,064,653 | 11/1991 | Sessions et al. | 424/445 |
| 5,066,427 | 11/1991 | Shroot et al. | 260/413 |

FOREIGN PATENT DOCUMENTS

| | | |
|---|---|---|
| 0539087A1 | 10/1992 | European Pat. Off. . |
| 3400106A1 | 1/1984 | Germany . |

*Primary Examiner*—Edward J. Webman
*Attorney, Agent, or Firm*—Carol J. Roth; Wendy L. Washtien; John L. White

[57] ABSTRACT

A topical bioadhesive ointment composition comprising an aqueous mineral oil emulsion which is readily spread able and film-forming, and, upon application to moist skin or a mucosal surface, forms a stable, coherent layer thereon which resists removal therefrom by water or a body fluid associated with the mucosal surface to which the ointment composition is applied is disclosed. Also disclosed are pharmaceutical compositions containing the ointment compositions and a pharmaceutically active agent, e.g., TGFα; and methods of using and methods of preparing the compositions.

39 Claims, No Drawings

TOPICAL BIOADHESIVE OINTMENT COMPOSITIONS AND THEIR USE IN WOUND HEALING

This application is a continuation-in-part of our application, Ser. No. 07/872,755, filed Apr. 23, 1992, abandoned, which is incorporated herein by its entirety by reference.

FIELD OF THE INVENTION

This invention is directed to bioadhesive ointment compositions, particularly to aqueous mineral oil emulsions which are viscous and film-forming and which are readily spreadable and adaptable to topical administration; to pharmaceutical compositions comprising the ointment compositions and a pharmaceutically active agent; and to their use, e.g., in the healing of wounds.

BACKGROUND OF THE INVENTION

Aqueous mineral oil emulsions have long been known and used in formulating topical cosmetic and pharmaceutical compositions. Generally speaking, bioadhesiveness, i.e., the ability of a thick coating to adhere tenaciously to moist skin or a mucosal surface to which it is applied, is not a particularly important functional requirement. However, one end-use area in which bioadhesiveness is an important factor is in pharmaceutical compositions which are applied to wounds to promote the healing thereof. Oftentimes, the fluid exudate from the wound tends to create a barrier between the pharmaceutically active agent or agents in the pharmaceutical composition applied to the wound, especially to the exposed surface area of the wound. Alternatively, the fluid exudate will physically dislodge the pharmaceutical composition from the wound area, particularly when the wound is on the inside of the mouth, where copious amounts of saliva usually are present. In the case of a covered wound, the exudate can promote the absorption of the pharmaceutical composition into the wound covering and away from the surface of the wound.

In general, aqueous mineral oil emulsions have poor bioadhesiveness and the more viscous they are, the more likely they are to not form a bond to the surface of the wound, particularly when the wound is moist. This problem of non-adherence is particularly acute in the case of wounds, ulcers and lesions on the inside of the mouth. The saliva present in the mouth often prevents even initial adherence of the emulsion to the wound area or rapidly causes dislodgement of the emulsion from the wound area.

It has now been found that certain aqueous mineral oil emulsions can be rendered bioadhesive by a combination of a hydratable particulate hydroxypropyl methylcellulose and a water-dispersible polymer which inhibits the hydration of the hydroxypropyl methylcellulose prior to the application of the emulsions to a wound area. It has further been found that these novel aqueous mineral oil emulsions are excellent vehicles for woundhealing promoters, particularly for growth factors such as TGFα.

SUMMARY OF THE INVENTION

In one aspect, this invention is directed to a topical bioadhesive ointment composition consisting of an aqueous mineral oil emulsion comprising water, about 20–45 % w/w mineral oil, an amount from about 5% to about 45% w/w of particulate hydroxypropyl methylcellulose effective to render the ointment composition bioadhesive, an amount from about 20% to about 55% w/w of a polyalkylene glycol effective to stabilize the emulsion by preventing its separation upon storage and to inhibit the hydration of the hydroxypropyl methylcellulose by the water present in the emulsion, and from 0–3% w/w non-ionic surfactant. The ointment composition, upon application to moist skin or a mucosal surface, forms a stable coherent film thereon which resists removal by water or a body fluid associated with the surface to which it is applied.

In another aspect, this invention is directed to a topical pharmaceutical composition comprising a topical bioadhesive ointment composition of the invention and an effective amount of a pharmaceutically active agent. The topical pharmaceutical composition, upon application to moist skin or a mucosal surface, forms a stable coherent film thereon which resists removal by water or a body fluid associated with the mucosal surface to which it is applied.

In another aspect, this invention is directed to a method of promoting the healing of a wound, ulcer or lesion on the skin or mucosal surface which comprises applying to the affected skin or mucosal surface a topical bioadhesive ointment composition of the invention.

In another aspect, this invention is directed to a method of promoting the healing of a wound, ulcer or lesion on the skin or mucosal surface which comprises applying to the affected skin or mucosal surface an effective amount of a topical pharmaceutical composition of the invention.

Upon further study of this specification and appended claims, further aspects and advantages of this invention will become apparent to those skilled in the art.

DETAILED DESCRIPTION OF THE INVENTION

A topical bioadhesive ointment composition of this invention is a viscous aqueous mineral oil emulsion which comprises water; mineral oil; a water-dispersible particulate hydrophilic hydroxypropyl methylcellulose suspended in the aqueous phase of the emulsion in an amount effective to form, when the emulsion is spread on a moist skin or mucosal surface, a stable, coherent film which resists removal therefrom by water or a body fluid associated therewith; a water-soluble polyalkylene glycol dissolved in the aqueous phase of the emulsion in an amount sufficient to reduce the water activity of the emulsion in order to retain the hydroxypropyl methylcellulose therein in particulate, non-fully hydrated form and to increase the viscosity thereof to a spreadable viscous paste; and, optionally, a non-ionic surfactant in an amount sufficient to render the emulsion stable for storage.

The ointment composition of this invention is characterized by being highly bioadhesive. As used herein, the term "bioadhesive" refers to the ability of a composition of the invention to persistently adhere to moist skin or mucosal surface when applied thereto with an adhesive bond which is at least as strong as the internal cohesive strength of the composition. The effect of the composition being bioadhesive is that the composition resists being physically wiped off the moist skin or mucosal surface to which it is applied or being washed off with a body fluid associated with the mucosal surface to which it is applied. The ability to be bioadhesive is particularly important in the compositions used in the oral mucosa because of the tongue's tendency to physically remove or dislodge any film or layer thereon.

An ointment composition of this invention is a viscous solid at temperatures which are at or around body temperature, i.e., about 37° C. Although the physical properties of the composition are temperature-dependent, at or near body temperature, the composition typically has a viscosity of at least 10,000, preferably at least 15,000, and more preferably about 19,000 centipoise. It is desirable that the composition is dispensed by extrusion from a toothpaste or ointment tube-type container, but it may also be dispensed in capsules or in jars. When spread on the skin or a mucosal surface, or a wound, lesion or ulcer therein, it forms a stable, coherent film. The inner surface of the film adheres strongly and persistently to the surface to which it is applied, thereby allowing the film to resist removal therefrom by physical means, water or by the body fluid associated with the mucosal surface, e.g., saliva. The outer surface of the film forms a tenacious barrier to the atmosphere which promotes healing and preferential diffusion of pharmaceutically active ingredients into the wound tissue rather than into mucosal fluids.

The mineral oil employed in the ointment compositions of this invention is preferably pharmaceutical grade. The mineral oil is present in an amount which produces an emulsion having the desired physical properties, i.e., about 20–45% w/w, preferably about 24–41% w/w, more preferably about 28–37% w/w, and most preferably at about 33.3% w/w. The amount of mineral oil and/or of the polyalkylene glycol present in the ointment compositions of the invention may be adjusted to provide the desired final viscosity.

Dispersed within the aqueous phase of the emulsion of the ointment compositions of the invention is a hydrophilic hydroxypropyl methylcellulose in particulate form, which, when hydrated with water, forms a tacky or sticky sol or gel. By being present in the emulsion in a suspended particulate form, rather than in hydrated sol or gel form, the hydroxypropyl methylcellulose renders the final composition bioadhesive, a property not generally possessed by ointment compositions comprised of an aqueous mineral oil emulsion. The particle size of the hydroxypropyl methylcellulose useful in this invention can vary substantially, e.g., from about 20 microns to about 400 microns. The pharmaceutical grades of hydroxypropyl methylcelluloses which are available commercially generally fall within this size range. Preferably, the hydroxypropyl methylcellulose used in the ointment compositions of the invention is commercially available from The Dow Chemical Company under the tradename METHOCEL® E10M. Other hydroxypropyl methylcelluloses may be used in the invention, provided, however, that the desired physical characteristics of the final compositions are maintained.

The hydroxypropyl methylcellulose is present in particulate form in the emulsion of the ointment composition of this invention in an amount from about 5–45% w/w, preferably from about 22–35% w/w, and most preferably at about 29%, effective to render the composition bioadhesive.

The polyalkylene glycol used in the ointment compositions of this invention is a member of a known class of α-hydro-ω-hydroxy-polyoxyalkylenes of the formula H[O-alkylene]$_m$-[O-alkylene]$_n$-OH, wherein the alkylene monomeric units can be the same or different, e.g., ethylene-1,2- and 1-3-propylene, and m and n are positive integers. The polyalkylene glycol can contain other monomeric units besides oxyalkylene in the molecule and/or its terminal hydroxy groups can be modified, provided the physical properties of the ointment composition as described herein are not adversely affected. Also, other hydrophilic polymeric equivalents of the polyalkylene polymers can be employed. Thus, contemplated equivalents of the compositions of this invention are those wherein the polyalkylene glycol component thereof is replaced partially or wholly by one of these functionally equivalent hydrophilic polymers.

The polyalkylene glycol is employed in the ointment compositions of this invention in an amount effective to stabilize the emulsion by preventing its separation upon storage. Such an amount will usually increase the final viscosity of the ointment composition substantially, e.g., to at least 11,000 centipoise. The polyalkylene glycol is also present in an amount effective to prevent the water in the emulsion from being absorbed by the hydrophilic hydroxypropyl methylcellulose present therein. In other words, the amount of polyalkylene glycol present in the compositions will decrease the water activity of the emulsion. This feature is critical to the usefulness of the ointment compositions of the invention. If the hydroxypropyl methylcellulose in the ointment composition were to become fully hydrated before the ointment composition is applied to the moist skin or mucosal surface, it loses its ability to render the composition bioadhesive. In particular, the polyalkylene glycol is present in an amount of about 20–55% w/w, preferably about 27–45% w/w, more preferably about 35–40% w/w, and most preferably at about 37% w/w, on a 100% solids per volume basis. These ranges translate to from about 41% to about 71%, preferably about 51–66%, and most preferably at about 61% (on a v/v basis) for a 35% aqueous solution.

The polyalkylene glycols employed in the ointment compositions of the invention can vary substantially in molecular weight, provided they are hydrophilic enough to be dispersible in water and thereby reduce the activity of the water in the emulsion. Preferably, the polyalkylene glycols are polyethylene glycols having a molecular weight in the range of 400 to 11,000, more preferably, in the range of 7,000 to 9,000. Most preferred is the polyethylene glycol having an average molecular weight of 8,000, e.g., PEG 8000, which is commercially available, e.g, from Aldrich Company.

The ointment compositions are optionally stabilized with the inclusion of a non-ionic surfactant, of which many are known in the art to be useful in producing stable aqueous emulsions in the cosmetic and pharmacy fields. See, e.g., Schwartz et al., "Surface Active Agents and Detergents," Vol. II, pp. 120–143 (Interscience Pub. Inc., N.Y., 1958). A preferred class of non-ionic surfactants are the polyoxyethylene (ethoxylates) surfactants in which a polyoxyethylene block polymer chain is terminated with a less soluble group, e.g., an alkylphenol ether group, an alcohol or mercaptan ether group, an amide group, or a carboxylic acid ester group, e.g., a surfactant of the formula

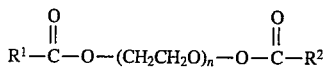

$$R^1-\overset{O}{\overset{\|}{C}}-O-(CH_2CH_2O)_n-O-\overset{O}{\overset{\|}{C}}-R^2$$

wherein n is between 5 and 25, and $R^1$ and $R^2$ are each a fatty acid chain of between 15 and 25 carbon atoms. A preferred group of non-ionic surfactants within this class are the polyoxyethylene sorbitan monoesters and triesters, which are commercially available under the trademark TWEEN®. These non-ionic surfactants are prepared by the addition of ethylene oxide to a 1,4-sorbitan monoester or triester. TWEEN® 80, which is otherwise known as polysorbate 80 or polyoxyethylene 20 sorbitan monooleate, is the most preferred non-ionic surfactant for use in the invention.

The non-ionic surfactant is present in the ointment compositions of the invention in a range from 0% to about 3% w/w, preferably from about 0.05 to 1.5% w/w, more preferably, at about 0.7% w/w.

In a preferred embodiment of this invention, the pharmaceutical compositions comprise the ointment composition and a pharmaceutically active agent, which can be a local anesthetic, e.g., benzocaine or xylocaine, and/or a compound known to promote the healing of wounds, e.g., a bacteriostat or bactericide, e.g., chloroxylenol or povidone-iodide, a sulfa drug, an antibiotic, fungislat or fungicide, e.g., tetracycline, nystatin or neomycin, an anti-inflammatory agent, e.g., zinc oxide and/or asteroid such as hydrocortisone, prednisolone, triamcinolone acetonide, halo-besterol propionate or beta-methasone dipropionate and/or a debriding agent, e.g., a proteolytic enzyme or biphenamine hydrochloride (U.S. Pat. No. 4,497,824), chemotherapeutic agents (when the composition is used to treat skin cancer, e.g., melanoma) e.g., fluorouracil, and growth factors, e.g., epidermal growth factors (EGF), nerve growth tactors (NGF), transforming growth factor (TGF), various colony stimulating factors (CSF), granulocyte/macrophage colony stimulating factors (G/M CSF), the interferons, the cytokines, such as the interleukins, e.g., lyphokines, ammonokines, and the like. In a preferred embodiment, the pharmaceutically active agent is TGF, particularly TGFα, which may be prepared as described in U.S. Pat. Nos. 4,816,561, 4,863,899 and 4,874,746.

The ointment compositions of this invention are topical in the sense that they are useful if applied to either moist skin or a mucosal surface. Thus, they can be employed to promote the healing of a variety of abnormal conditions of the skin and mucosal membranes, e.g., wounds, ulcers and lesions associated with infected or traumatic wounds; thermal, electrical, chemical and traumatic bums; scrapes, abrasions; lesions associated with the urogenital tract; the tongue, the inside of the mouth or gingiva, the face, eye, nose, sinus, bacterial and fungal infections, especially those which produce lesions; athlete's foot which produces fissures or lesions in the skin; plantar warts; varicose ulcers; leg ulcers from impaired circulation; hemorrhoids and fissures in the colon; oral surgery; pimples, pustules or infected areas produced by splinters or other foreign bodies; bladder inflammations; senile keratosis; human, animal and insect bites; and any other wound, whether benign or malignant, sterile or infected with bacteria, virus or fungus, and psoriasis, seborrhea, pururitis, pigmentatious abnormalities and skin cancer, particularly when it contains a pharmaceutically active agent.

The ointment compositions of this invention are particularly suited for the treatment of oral mucositis, which is a condition which frequently accompanies radiation or chemotherapy. A mucous membrane typically is formed of fast-growing cells which divide quickly and, like cancerous cells, tend to be killed by the therapy treatments. As a result, lesions in the mucous membrane often arise, for which an effective treatment has not heretofore been developed. Therefore, in a preferred aspect, this invention is directed to the treatment of oral mucositis, particularly when associated with cancer therapy.

To treat a wound or ulcerated area of the skin or a mucosal surface, e.g., the inside of the mouth, the ointment compositions of this invention (with or without the presence of a pharmaceutically active agent) are applied topically, preferably on successive occasions, e.g., as frequently as every hour or as infrequently as daily or longer, depending on the severity and intractability of the pathological condition. It is desirable to apply the ointment composition promptly after the wound, lesion or ulcer appears or is inflicted and on successive occasions thereafter, e.g., once every 2–12 hours for 2–14 days or until the wound, lesion or ulcer is healed. Because the ointment composition is film-forming upon application, it forms a coating over the wound, lesion or ulcer. Such coating acts as a barrier to the atmosphere and sources of further irritation and/or infection, thereby promoting healing, even in the absence of a pharmaceutically active agent therein. For this reason, the ointment composition of the invention can be used by itself without the presence of a pharmaceutically active agent to promote the healing of internal wounds, e.g., stomach ulcers.

The ointment compositions of this invention can also be used topically to ameliorate pain not associated with a wound, ulcer or lesion, e.g., a bruised area of the skin, in which case an anti-inflammatory agent, skin penetrant and/or local anesthetic as the pharmaceutically active agent is desirably present therein.

The effective amount of the ointment composition or the pharmaceutical compositions of the invention applied to the affected area will depend on such factors as the degree or localization thereof, the concentration of pharmaceutically active agent therein, the individual's responsiveness to the therapy and the amounts thereof required to cover the affected area. Generally, enough ointment composition to provide a coating over the affected area of about 1–6 mm thick per application is effective. The effectiveness of successively greater or smaller dosages can determine the optimum effective individual dose.

Because of the heat labile nature of some pharmaceutically active agents and most biologics, including TGFα, the desired agents are advantageously sterile mixed with the previously sterilized ointment composition, since post-sterilization by gamma radiation tends to reduce the viscosity of the sterilized final pharmaceutical composition to an unacceptably low level. The ointment composition can be sterilized in a conventional manner, e.g., at 110°–125° C. for 10–30 minutes in an autoclave.

The sterile ointment composition can then be sterile-filled in a conventional manner into jars or ointment collapsible dispensing tubes and thereafter autoclaved and thereafter sealed therein or post-sterilized after filling. The ointment composition can then be sterile-mixed with the desired pharmaceutically active agent, e.g., TGFα, and thereafter sterile-filled into the desired dispensing container.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and except where indicated, all parts and percentages are by weight/weight (w/w).

The entire disclosure of all applications, patents and publications cited herein are hereby incorporated by reference.

EXAMPLE 1

Preparation of Ointment Composition

Dissolve polyethylene glycol-8000 (PEG 8000, 35 g, Dow Chemicals, Inc.) in distilled water and bring the final volume to 100 mL. Add 0.45 g of Tween 80 to the thus-produced 35% (w/v) PEG 8000 solution and completely dissolve therein at 80° C. Mix 19.36 g mineral oil with the Tween 80 and PEG-8000 mixture in a Polytron homogenizer until a milk-white emulsion is formed. Add 17 g hydroxypropyl methylcellulose (METHOCEL® E10M, Dow Chemicals, Inc.) to the emulsion in the Polytron homogenizer with vigorous mixing. The resulting ointment composition (hereinafter referred to by the arbitrary designation "TJ" or "TJ formulation") has the following composition:

| | |
|---|---|
| Mineral Oil | 33.3% |
| Tween 80 | 0.7% |
| PEG-8000 (35% wt/v in $H_2O$) | 36.7% |
| METHOCEL ® E10M | 29.3% |

EXAMPLE 2

Preparation of Sterile Pharmaceutical Composition Containing TGFα

Sterilize 5.0 g of the ointment composition prepared in Example 1 in a 20 mL glass vial by autoclaving at 121° C. for 15 minutes. Under sterile conditions, cool to 4° C. and add thereto an amount of α-transforming growth factor (TGFα) appropriate for the intended enduse, typically a submilligram amount per milliliter, e.g., 25 μg TGFα/0.25 mL of ointment composition, and mix thoroughly. Sterile bottom fill into a 5 cc capped ointment dispensing tube. Crimp close the bottom of the filled tube in the conventional manner.

The thus-prepared TGFα-containing ointment composition has highly desirable properties, including (1) bioadherence to oral mucous membrane; (2) sustained release of the TGFα therefrom; (3) comfortable administration thereof to an ulceration wound; (4) complete in situ release of the TGFα therefrom; (5) autoclave sterilizability of the ointment composition; and (6) retention of the TGFα therein in a bioactive form.

EXAMPLE 3

In vitro and in vivo assays

The TGFα-containing ointment composition of Example 2 (TJ-TGFα formulation) was subjected, both in vitro and in vivo, to evaluation to meet the therapeutical requirements for oral mucositis. The in vitro evaluation included TGFα release and extraction from the composition, autoclave sterilizability and the bioactivity and stability of TGFα in the composition. The in vivo evaluation included TGFα uptake and tissue distribution of absorbed TGFα from hamster's cheek pouch.

A. The in vitro extractability of the TGFα from the TJ-TGFα formulation was determined both by exhaustive extraction of the mineral oil from the formulation followed by reverse phase HPLC analysis of the extracted TGFα and by extraction at one-hour intervals of successive aliquots of PBS buffer of a 5:1 mixture of TGFα and C-14 labeled TGFα and measuring the radioisotope levels of the successive PBS buffer extracts.

The following are the results of the this determination:

| Release Rate of TGFα Released from TJ-TGFα Formulation | | | | | |
|---|---|---|---|---|---|
| | TJA-1 | TJA-2 | TJA-3 | X̄ | S |
| 0 hrs. | 10% | 6.0% | 10% | 8.6% | 2.3 |
| 1 hr. | 36% | 33% | 36% | 35% | 1.7 |
| 2 hrs. | 49% | 50% | 51% | 50% | 1.0 |
| 3 hrs. | 63% | 56% | 59% | 59% | 3.5 |
| 5 hrs. | 70% | 78% | 82% | 76% | 6.1 |
| 7 hrs. | 78% | 90% | 87% | 85% | 6.2 |

| Release Rate of TGFα Released from TJ-TGFα Formulation | | | | | |
|---|---|---|---|---|---|
| | TJ-1 | TJ-2 | TJ-3 | X̄ | S |
| 0 hrs. | 8.0% | 6.0% | 6.0% | 6.6% | 1.1 |
| 1 hr. | 31% | 29% | 31% | 30% | 1.1 |
| 2 hrs. | 39% | 38% | 42% | 39% | 2.0 |
| 3 hrs. | 48% | 46% | 48% | 47% | 1.1 |
| 5 hrs. | 63% | 60% | 64% | 62% | 2.0 |
| 7 hrs. | 72% | 71% | 71% | 71% | 0.5 |

TJA-1, TJA-2 and TJA-3: Autoclaved TJ-TGFα formulations
TJ-1, TJ-2 and TJ-3: non-autoclaved TJ-TGFα formulations The storage stability of the TGFα in the TJ-TGFα formulation was determined at room temperature and at 4° C. after 48 hours and after 4 days by extracting the TGFα after the test in PBS buffer and testing for residual bioactivity by conventional membrane radioreceptor assay. The results of these bioactivity and stability studies are as follows:

(i) Bioactivity:

| TJ-TGFα formulation, autoclaved | TJ-TGFα formulation, non-autoclave |
|---|---|
| 86% | 60% |

(ii) Stability:

| 48 hrs. Room Temp. | 48 hrs. 4° C. | 8th day 4° C. | 8th day Room Temp. |
|---|---|---|---|
| 51% | 67% | 56% | 39% |

B. The in vivo uptake of TGFα from the TJ-TGFα formulation was determined in Golden Syrian hamsters, female, approximately 150 g using an $^{125}$I-TGFα formulation (specific activity-45 μci/μg), the hamster's cheek pouch having a mechanically created wound. A pharmacokinetic study of tissue distribution of TGFα absorbed by the hamsters was also conducted. The methods employed were as follows:

1. Fast hamsters overnight.
2. Anesthetize hamsters by I.M. injection of ketamine HCl.
3. Create a 2 mm diameter wound on the right-hand side of hamster's cheek pouch by a biopsy punch.
4. Following the removal of the debridement and blood clot, administer 20 μl TJ-TGFα formulation containing 26 μci 125I-TGFα onto the wound area by a Gilson Microman.
5. Keep the hamsters in their cages and give no water or food during the course of 6 hours study.
6. Select three hamsters at time 15 minutes, 30 minutes, 1 hour, 2 hours, 4 hours and 6 hours and select one hamster at 24 hours for TGFα uptake and tissue distribution study.
7. Punch a needle into the hamster's heart and withdrawn 1 ml blood by a 5 ml syringe.
8. Sacrifice hamster by inhalation of an overdose of carbon dioxide vapor from dry ice in a closed chamber.
9. Immediately after sacrificing, remove the liver, kidney, thyroid, submaxillary gland, esophagus, stomach, small intestine, cecum, colon, 25 $cm^2$ skin on back, tongue and right-hand side of cheek pouch.
10. Flush the contents of esophagus, stomach, small intestine and cecum with water and collect the contents separately into a test tube.
11. Count the CPM of $^{125}$I-TGFα that distributed in the hamster's tissue and GI contents.

The results of such a tissue distribution study are shown in TABLE 1 and TABLE 2 as follows:

TABLE 1

| | Distribution of $^{125}$I-TGFα in the Tissues | | | | | | |
|---|---|---|---|---|---|---|---|
| | 15 min. | 0.5 hrs. | 1 hr. | 2 hrs. | 4 hrs. | 6 hrs. | 24 hrs. |
| Blood | 0.01% | 0.02% | 0.04% | 0.05% | 0.13% | 0.13% | 0.22% |
| Liver | 0.03% | 0.07% | 0.09% | 0.17% | 0.26% | 0.24% | 0.59% |
| Kidney | 0.02% | 0.07% | 0.07% | 0.14% | 0.23% | 0.27% | 0.24% |
| Thyroid | 0.005% | 0.02% | 0.02% | 0.14% | 0.39% | 0.88% | 2.84% |
| Submaxillary Gland | 0.02% | 0.05% | 0.04% | 0.20% | 0.42% | 0.77% | 0.77% |
| Esophagus | 0.001% | 0.01% | 0.01% | 0.01% | 0.26% | 0.27% | 0.04% |
| Stomach | 0.01% | 0.03% | 0.05% | 0.10% | 0.74% | 1.06% | 1.23% |
| Small Intestine | 0.01% | 0.05% | 0.04% | 0.07% | 0.12% | 0.15% | 0.40% |
| Cecum | 0.303% | 0.01% | 0.02% | 0.06% | 0.04% | 0.08% | 0.05% |
| Colon | 0.01% | 0.02% | 0.04% | 0.06% | 0.13% | 0.12% | 1.57% |
| Skin | 0.04% | 0.06% | 0.03% | 0.10% | 0.14% | 0.13% | 0.13% |
| Tongue | 0.85% | 3.13% | 4.82% | 3.57% | 3.37% | 1.25% | 0.66% |
| Cheek Pouch | 76% | 30% | 70% | 74% | 74% | 84% | 21% |

TABLE 2

| | Distribution of $^{125}$I-TGFα in the GI Contents | | | | | | |
|---|---|---|---|---|---|---|---|
| | 15 min. | 0.5 hrs. | 1 hr. | 2 hrs. | 4 hrs. | 6 hrs. | 24 hrs. |
| Esophagus | 0.00005% | 0.01% | 0.002% | 0.01% | 0.37% | 0.27% | 0.01% |
| Stomach | 0.03% | 0.056% | 0.20% | 0.40% | 4.1% | 7.8% | 5.5% |
| Small Intestine | 0.003% | 0.01% | 0.02% | 0.02% | 0.06% | 0.05% | 0.52% |
| Cecum | 0.003% | 0.01% | 0.02% | 0.02% | 0.04% | 0.05% | 2.63% |

The preceding examples can be repeated with similar success by substituting the generically or specifically described reactants and/or operating conditions of this invention for those used in the preceding Examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A topical bioadhesive ointment composition consisting of an aqueous mineral oil emulsion comprising about 20–45% w/w mineral oil, an amount from about 5% to about 45% w/w of particulate hydroxypropyl methylcellulose effective to render the ointment composition bioadhesive, an amount from about 27% to about 45% w/w of polyalkylene glycol (35% w/v in water) effective to stabilize the emulsion by preventing its separation upon storage and to inhibit the hydration of the hydroxypropyl methylcellulose by the water present in the emulsion, and from 0–3% w/w non-ionic surfactant; wherein the ointment composition, upon application to moist skin or a mucosal surface, forms a stable coherent film thereon which resists removal by water or a body fluid associated with the skin or the mucosal surface to which it is applied.

2. The composition of claim 1 wherein the polyalkylene glycol has a molecular weight in the range of from about 400 to about 11,000 D.

3. The composition of claim 2 wherein the polyalkylene glycol is a polyethylene glycol.

4. The composition of claim 3 wherein the polyethylene glycol is PEG 8000.

5. The composition of claim 1 wherein the mineral oil content thereof is from about 24% w/w to about 41% w/w.

6. The composition of claim 5 wherein the mineral oil content thereof is about 33.3% w/w.

7. The composition of claim 1 wherein the polyalkylene glycol content thereof is about 37% w/w.

8. The composition of claim 1 wherein the hydroxypropyl methylcellulose content thereof is from about 22% to about 35% w/w.

9. The composition of claim 8 wherein the hydroxypropyl methylcellulose content thereof is about 29.3% w/w.

10. The composition of claim 1 wherein the non-ionic surfactant content thereof is from about 0.05% to about 1.5% w/w.

11. The composition of claim 1 having a viscosity of at least 10,000 centipoise.

12. The composition of claim 1 having a viscosity of about 19,000 centipoise.

13. The composition of claim 1 which comprises from about 24% to about w/w mineral oil; from about 22% to about 35% w/w hydroxypropyl methylcellulose; and from about 27% to about 45% w/w polyethylene glycol; and which has a viscosity of at least 10,000 centipoise.

14. The composition of claim 13 which comprises about 33.3% w/w mineral oil; about 37% w/w polyethylene glycol; from about 0.05% to about 1.5% w/w polyoxyethylene 20 sorbitan monooleate; about 29.3% w/w hydroxypropyl methylcellulose; and which has a viscosity of at least about 19,000 centipoise.

15. The composition of claim 13 wherein the polyethylene glycol is PEG 8000 and the hydroxypropyl methylcellulose is METHOCEL® E10M.

16. A topical pharmaceutical composition comprising:

a) a bioadhesive ointment composition consisting of an aqueous mineral oil emulsion comprising about 20–45% w/w mineral oil, an amount from about 5% to about 45% w/w of particulate hydroxypropyl methylcellulose effective to render the ointment composition bioadhesive, an amount from about 27% to about 45% w/w of polyalkylene glycol (35% w/v in water) effective to stabilize the emulsion by preventing its separation upon storage and to inhibit the hydration of the hydroxypropyl methylcellulose by the water present in the emulsion, and from 0–3% w/w non-ionic surfactant; and b) an effective amount of a pharmaceutically active agent; wherein the topical pharmaceutical composition, upon application to moist skin or a mucosal surface, forms a stable coherent film thereon which resists removal by water or a body fluid associated with the skin or the mucosal surface to which it is applied.

17. The pharmaceutical composition of claim 16 wherein the pharmaceutically active agent is a local anesthetic.

18. The pharmaceutical composition of claim 16 wherein the pharmaceutically active agent is TGFα.

19. The pharmaceutical composition of claim 16 wherein the polyalkylene glycol has a molecular weight in the range of from about 400 to about 11,000 D.

20. The pharmaceutical composition of claim 19 wherein the polyalkyene glycol is a polyethylene glycol.

21. The pharmaceutical composition of claim 20 wherein the polyethylene glycol is PEG 8000.

22. The pharmaceutical composition of claim 16 wherein the mineral oil content thereof is from about 24% w/w to about 41% w/w.

23. The pharmaceutical composition of claim 22 wherein the mineral oil content thereof is about 33.3% w/w.

24. The pharmaceutical composition of claim 16 wherein the polyalkylene glycol content thereof is about 37% w/w.

25. The pharmaceutical composition of claim 24 wherein the hydroxypropyl methylcellulose content thereof is from about 22% to about 35% w/w.

26. The pharmaceutical composition of claim 16 wherein the hydroxypropyl methylcellulose content thereof is about 29% w/w.

27. The pharmaceutical composition of claim 16 wherein the non-ionic surfactant content thereof is from about 0.05% to about 1.5% w/w.

28. The pharmaceutical composition of claim 16 having a viscosity of at least 10,000 centipoise.

29. The pharmaceutical composition of claim 28 having a viscosity of about 19,000 centipoise.

30. The pharmaceutical composition of claim 16 which comprises from about 24% to about 41% w/w mineral oil; from about 22%–35% w/w hydroxypropyl methylcellulose; and from about 27%–45% w/w polyethylene glycol; and which has a viscosity of at least 10,000 centipoise.

31. The pharmaceutical composition of claim 30 which comprises about 33.3% w/w mineral oil; about 29.3% w/w hydroxypropyl methylcellulose; about 37% w/w polyethylene glycol [(35% w/v in water)]; from about 0.05% to about 1.5% w/w polyoxyethylene 20 sorbitan monooleate; and which has a viscosity of about 19,000 centipoise.

32. A method of promoting the healing of a wound, ulcer or lesion on the skin or mucosal surface which comprises applying to the affected skin or mucosal surface a topical bioadhesive ointment composition, wherein the ointment composition consists of an aqueous mineral oil emulsion comprising about 20–45% w/w mineral oil, an amount from about 5% to about 45% w/w of particulate hydroxypropyl methylcellulose effective to render the ointment composition bioadhesive, an amount from about 27% to about 45% w/w of polyalkylene glycol (35% w/v in water) effective to stabilize the emulsion by preventing its separation upon storage and to inhibit the hydration of the hydroxypropyl methylcellulose by the water present in the emulsion, and from 0–3% w/w non-ionic surfactant; wherein the ointment composition, upon application to moist skin or a mucosal surface, forms a stable coherent film thereon which resists removal by water or a body fluid associated with the skin or the mucosal surface to which it is applied.

33. A method of promoting the healing of a wound, ulcer or lesion on the skin or mucosal surface which comprises applying to the affected skin or mucosal surface an effective amount of a topical pharmaceutical composition, wherein the pharmaceutical composition comprises:

a) a bioadhesive ointment composition consisting of an aqueous mineral oil emulsion comprising about 20–45% w/w mineral oil, an amount from about 5% to about 45% w/w of particulate hydroxypropyl methylcellulose effective to render the ointment composition bioadhesive, an amount from about 27% to about 45% w/w of polyalkylene glycol (35% w/v in water) effective to stabilize the emulsion by preventing its separation upon storage and to inhibit the hydration of the hydroxypropyl methylcellulose by the water present in the emulsion, and from 0–3% w/w non-ionic surfactant; and b) an effective amount of a pharmaceutically active agent; wherein the topical pharmaceutical composition, upon application to moist skin or a mucosal surface, forms a stable coherent film thereon which resists removal by water or a body fluid associated with the skin or the mucosal surface to which it is applied.

34. The method of claim 33 which comprises about 33.3% w/w mineral oil; about 37% w/w polyethylene glycol; about 29.3% w/w hydroxypropyl methylcellulose; about 0.05% to about 1.5% w/w polyoxyethylene 20 sorbitan monooleate; and which has a viscosity of at least about 19,000 centipoise.

35. The method of claim 34 wherein the pharmaceutically active agent is a local anesthetic.

36. The method of claim 34 wherein the pharmaceutically active agent is TGFα.

37. The method of claim 33 wherein the affected area is the inside of the mouth.

38. The method of claim 37 wherein the pharmaceutical composition is applied to the affected area at least once a day on a plurality of successive days.

39. The method of claim 33 wherein the pharmaceutical composition is applied to the affected area on successive occasions.

* * * * *